(12) United States Patent
Xiao et al.

(10) Patent No.: US 12,196,627 B2
(45) Date of Patent: Jan. 14, 2025

(54) STRETCHABLE, REHEALABLE, RECYCLABLE AND RECONFIGURABLE INTEGRATED STRAIN SENSOR

(71) Applicant: THE REGENTS OF THE UNIVERSITY OF COLORADO, A BODY CORPORATE, Denver, CO (US)

(72) Inventors: Jianliang Xiao, Louisville, CO (US); Wei Zhang, Boulder, CO (US); Chuanqian Shi, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 164 days.

(21) Appl. No.: 17/574,880

(22) Filed: Jan. 13, 2022

(65) Prior Publication Data
US 2022/0221354 A1    Jul. 14, 2022

Related U.S. Application Data

(60) Provisional application No. 63/136,714, filed on Jan. 13, 2021.

(51) Int. Cl.
*G01L 1/22* (2006.01)
*A61B 5/00* (2006.01)
*G01L 1/20* (2006.01)

(52) U.S. Cl.
CPC .......... *G01L 1/2287* (2013.01); *A61B 5/6843* (2013.01); *G01L 1/205* (2013.01)

(58) Field of Classification Search
CPC ...... G01L 1/2287; G01L 1/205; A61B 5/6843
See application file for complete search history.

(56) References Cited

U.S. PATENT DOCUMENTS

| 4,325,048 A | * | 4/1982 | Zaghi | G01L 1/2225 |
| | | | | 73/862.634 |
| 9,613,911 B2 | * | 4/2017 | Rogers | H01L 23/538 |
| 11,590,006 B2 | * | 2/2023 | Xiao | A61F 2/586 |
| 2014/0220422 A1 | * | 8/2014 | Rogers | H01L 23/18 |
| | | | | 438/117 |

(Continued)

FOREIGN PATENT DOCUMENTS

| CN | 108085519 A | * | 5/2018 | ................ B22F 9/06 |
| WO | 2016118536 A2 | | 7/2016 | |

OTHER PUBLICATIONS

CN108085519 machine translation. (Year: 2018).*

(Continued)

*Primary Examiner* — Kyung S Lee
(74) *Attorney, Agent, or Firm* — Saul Ewing LLP; Kathryn Doyle; Domingos Silva

(57) ABSTRACT

The present disclosure provides a high-performance integrated strain sensing device that is highly stretchable, rehealable, recyclable and reconfigurable. This device can include dynamic covalent thermoset polyimine as the substrate and encapsulation, eutectic liquid metal alloy as the strain sensing unit and interconnects, and off-the-shelf chip components for measuring and magnifying functions. The device can be attached on the knee, elbow, wrist and finger joints for strain sensing and motion monitoring, and can also be attached on the abdomen to accurately measure respiration cycles.

10 Claims, 19 Drawing Sheets

(56) References Cited

U.S. PATENT DOCUMENTS

| | | | |
|---|---|---|---|
| 2017/0365557 A1* | 12/2017 | Rogers | H05K 1/0283 |
| 2018/0143091 A1* | 5/2018 | Wood | G06F 3/014 |
| 2018/0254566 A1 | 9/2018 | Holbery et al. | |
| 2020/0291164 A1 | 9/2020 | Xiao et al. | |
| 2020/0296825 A1* | 9/2020 | Ozdoganlar | H05K 3/388 |
| 2022/0256711 A1* | 8/2022 | Xiao | H01L 25/04 |

OTHER PUBLICATIONS

Adzima, et al., "Externally Triggered Healing of a Thermoreversible Covalent Network via Self-Limited Hysteresis Heating", Adv. Mater., 22, 2784, 2010.

Guder, et al., "Paper-Based Electrical Respiration Sensor", Angew. Chemie Int. Ed., 55, 5727, 2016.

Hwang, et al., "A Physically Transient Form of Silicon Electronics, With Integrated Sensors, Actuators and Power Supply", Science, 337, 1640, 2012.

Kim, et al., "Fabrication of a Stretchable Solid-State Micro-Supercapacitor Array", ACS Nano, 7, 7975, 2013.

Kim, et al., "Materials and noncoplanar mesh designs for integrated circuits with linear elastic responses to extreme mechanical deformations.", Proceedings of the National Academy of Sciences of the United States of America 105, 2008, 18675-18680.

Lei, et al., "Biocompatible and totally disintegrable semiconducting polymer for ultrathin and ultralightweight transient electronics", Proc. Natl. Acad. Sci. U. S. A., 114, 5107, 2017.

Li, et al., "A highly stretchable autonomous self-healing elastomer.", Nat Chem 8, 2016, 618-624.

Lipomi, et al., "Skin-like pressure and strain sensors based on transparent elastic films of carbon nanotubes", Nat. Nanotechnol., 6, 788., 2011.

Lu, et al., "Sacrificial Synthesis of Supported Ru Single Atoms and Clusters on N-doped Carbon Derived from Covalent Triazine Frameworks: A Charge Modulation Approach", Adv. Mater., 31, 1., 2019.

Lumbroso, et al., "The effect of kinesio tape application on hamstring and gastrocnemius muscles in healthy young adults", Bodyw. Mov. Ther., 18, 130, 2014.

Nikitczuk, et al., "Control of electro-rheological fluid based resistive torque elements for use in active rehabilitation devices", Smart Mater. Struct., 16, 418, 2007.

Oh, et al., "Intrinsically stretchable and healable semiconducting polymer for organic transistors.", Nature 539, 2016, 411-415.

Rullyani, et al., "Flexible Organic Thin Film Transistors Incorporating a Biodegradable CO2-Based Polymer as the Substrate and Dielectric Material", Sci. Rep., 8, 1., 2018.

Shi, et al., "A Conductive Self-healing Hybrid Gel Enabled by Metal-ligand Supramolecule and Nanostructured Conductive Polymer", Nano Lett., 15, 6276, 2015.

Shi, et al., "Heterogeneous integration of rigid, soft, and liquid materials for self-healable, recyclable, and reconfigurable wearable electronics", Science Advances, vol. 6, Nov. 6, 2020, 1-8.

Tee, et al., "An electrically and mechanically self-healing composite with pressure- and flexion-sensitive properties for electronic skin applications.", Nat Nanotechnol 7, 2012, 825-832.

Toohey, et al., "Self-healing materials with microvascular networks.", Nature materials 6, 581-585, 2007, 581-585.

Wang, et al., "Continuous Monitoring and Modeling Contractility of Skeletal Muscles in Motion", Med. Res. Arch., 6, 1, 2018.

Woollard, et al., "4 Shortness of Breath", Emerg. Med. J., 21, 341, 2004.

Xu, et al., "Soft microfluidic assemblies of sensors, circuits, and radios for the skin.", Science 344, 2014, 70-74.

Zhang, et al., "Buckling in serpentine microstructures and applications in elastomer-supported ultra-stretchable electronics with high areal coverage", Soft Matter, 9, 8062, 2013.

Zhang, et al., "Mechanics of ultra-stretchable self-similar serpentine interconnects", Acta Mater., 61, 7816, 2013.

Zou, et al., "Rehealable, fully recyclable, and malleable electronic skin enabled by dynamic covalent thermoset nanocomposite", Science Advances, vol. 4, No. 2, Feb. 9, 2018, pp. 1-7.

\* cited by examiner (a) Vertically stretched by 60%

(c) Biaxially stretched by 30%

(b) Horizontally stretched by 60%

(d) Reconfiguration

STRETCHABLE, REHEALABLE, RECYCLABLE AND RECONFIGURABLE INTEGRATED STRAIN SENSOR

CROSS-REFERENCE TO RELATED APPLICATION(S)

This application claims priority under 35 U.S.C. § 119(e) to U.S. Provisional Patent Application Ser. No. 63/136,714, filed Jan. 13, 2021. The entire content of this application is hereby incorporated by reference herein.

STATEMENT REGARDING FEDERALLY SPONSORED RESEARCH OR DEVELOPMENT

This invention was made with government support under grant number CMMI1762324 awarded by the National Science Foundation. The government has certain rights in the invention.

BACKGROUND OF THE INVENTION

Cutting-edge technologies of stretchable, skin-mountable, and wearable electronics attract attention due to their wide applications and performances. One direction of particular interest is to investigate stretchable electronics with multi-functional materials.

SUMMARY

Stretchable, rehealable, recyclable, and reconfigurable integrated strain sensors are described herein. In one aspect, a strain sensing device can include a volume of liquid metal (LM); a polyimine film encapsulating the volume of LM in a defined channel; and a monitoring circuit encapsulated by the polyimine film and electrically coupled to the volume of LM, where the monitoring circuit is configured to: determine a change in a property of the volume of LM; and identify a strain value of the polyimine film from the determined change.

This aspect can include a variety of embodiments. In some embodiments, the property of the volume of LM can include a resistance of the volume of LM. In other embodiments, the volume of LM can be doped with microparticles. In some cases, the microparticles can be composed of silicon dioxide.

In other embodiments, the monitoring circuit can be a Wheatstone bridge. In other embodiments, the monitoring circuit can be electrically coupled to the volume of LM via a set of LM leads.

In other embodiments, individual components of the monitoring circuit are electrically coupled to one another with a set of LM leads. In other embodiments, the strain sensing device can further include at least one LED electrically connected to the monitoring circuit. In some cases, the LED is configured to emit light at a predefined strain value threshold.

In other embodiments, the strain sensing device is configured to be coupled to a joint of a patient.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 5 (comprising Panels (a)-(g)) depicts joint motion and respiration monitoring images and graphs according to embodiments of the present disclosure. The strain sensor is attached on a knee in Panel (a), an elbow in Panel (b), and a wrist in Panel (c) for monitoring the strains induced by joint flexion. Panel d) depicts the strain sensor attached on an index finger for sensing the strains induced by holding objects of difference sizes. Panel (e) depicts the strain sensor attached on a knee detecting different states of physical activities, including squatting, flexing, jumping and walking. Panel (f) depicts the strain sensor attached on the abdomen for monitoring respiration. Panel (g) depicts the integrated strain sensor attached on an elbow. When the elbow is not flexing (left subpanel), or the flexion angle is small (middle subpanel), the LED stays off. When the elbow flexion angle is too large (right subpanel), the LED turns on.

DEFINITIONS

Figure 1A:
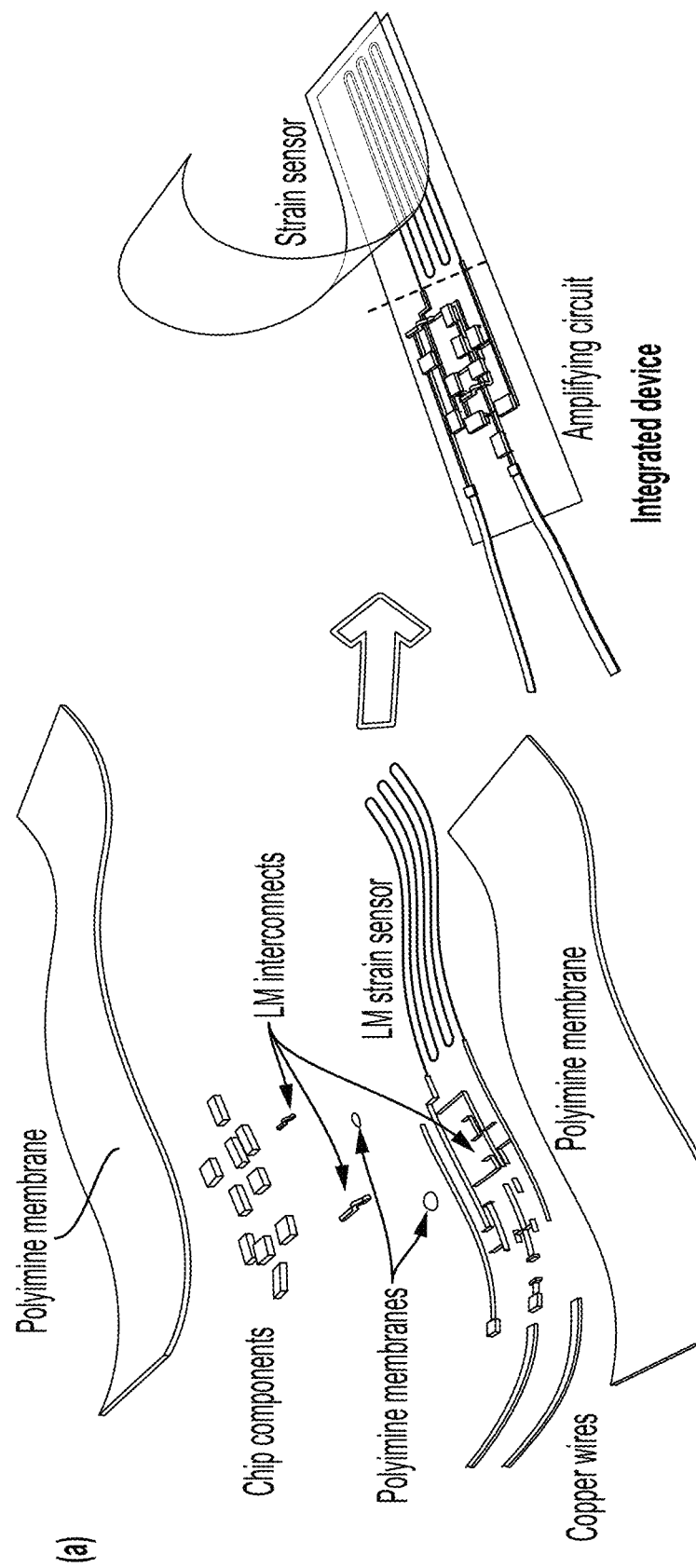
FIG. 1 (comprising Panels (a)-(f)) depicts design and construction of a stretchable strain sensing system according to embodiments of the present disclosure. Panel (a) depicts an exploded view of the strain sensing system. Optical images of the amplifying circuit in its undeformed state is depicted in Panel (b); a bent state in Panel (c); and a twisted state in Panel (d). Panel (e) depicts a reconfiguration of the amplifying circuit. Panel (f) depicts a strain sensing system attached on an elbow for monitoring its flexion states. When the elbow is straight, the LED is off (top subpanel). When the elbow flexes beyond a threshold, the LED turns on (bottom subpanel).
Figures 1B, 1C, 1D, 1E, 1F:
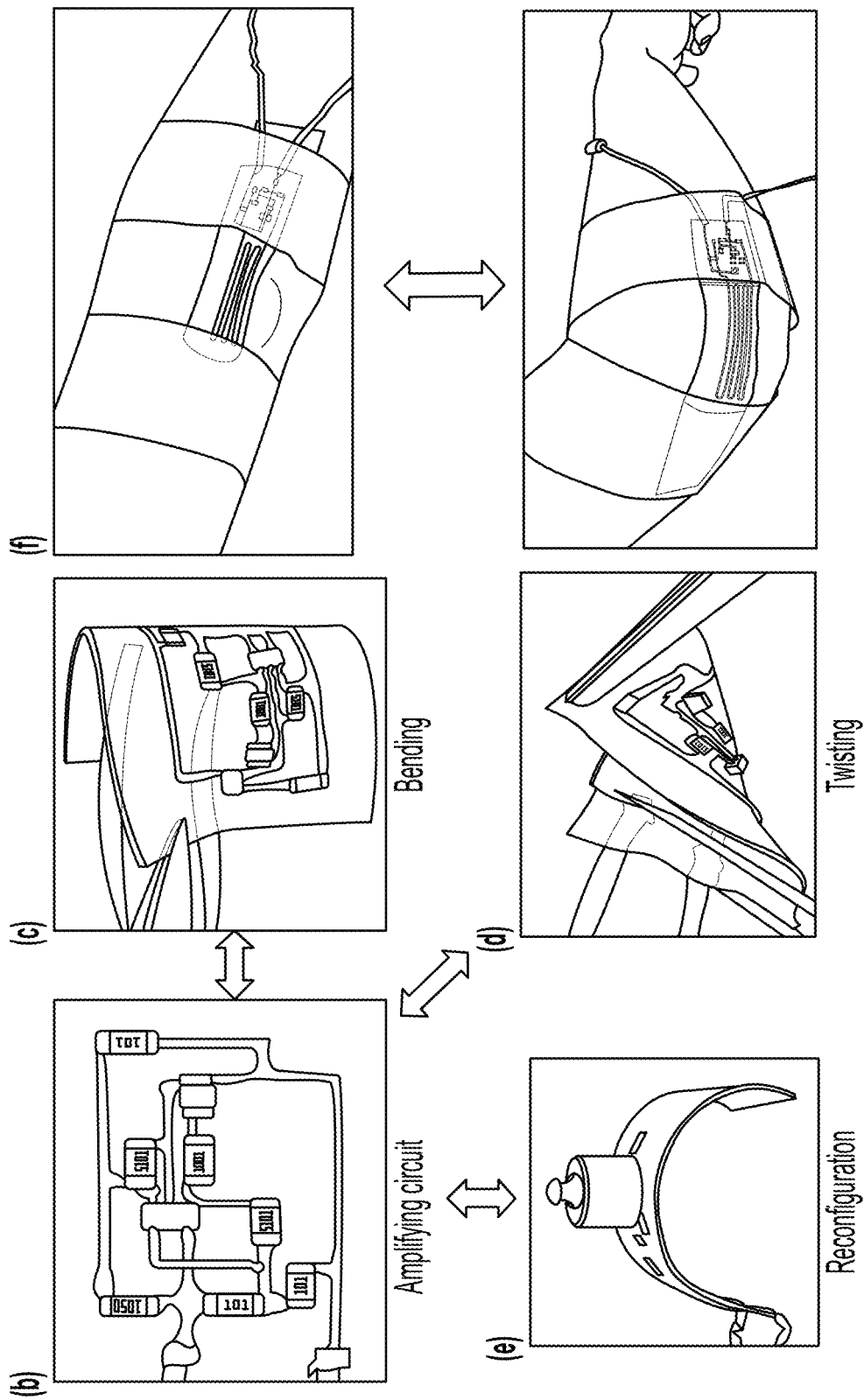

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Soft and stretchable integrated electronic systems show superior mechanical compliance and deformability, and thus can be applied in unusual places that are not possible for conventional rigid electronics, such as bio-inspired imagers, bio-integrated electronics for diagnosis and drug delivery, and electronic skins for health monitoring and virtual reality. To achieve electronic performances comparable to the established semiconductor devices, off-the-shelf chip components can be integrated with soft, stretchable substrates through mechanical designs that can effectively shield strains in brittle electronic components from the soft substrates experiencing large deformation. For mechanical attributes, ultralow modulus and high stretchability were accomplished by functional/hyperelastic materials, buckled metal traces, and liquid interconnects. More recently, materials with self-healing capabilities have also been adopted in developing self-healable electronics to mimic naturel skin. In order to avoid surgical removal of medical implants, to protect security of hardware and data, or to reduce electronic waste, transient, degradable and recyclable electronic systems were developed by using materials that can be physically eliminated within a specified period of time.

Embodiments of the present disclosure introduce a high-performance integrated strain sensing device that is highly stretchable, rehealable, recyclable and reconfigurable. This device can include dynamic covalent thermoset polyimine as the substrate and encapsulation, eutectic liquid metal alloy as the strain sensing unit and interconnects, and off-the-shelf chip components for measuring and magnifying functions. The device can be attached on the knee, elbow, wrist and finger joints for strain sensing and motion monitoring, and can also be attached on the abdomen to accurately measure respiration cycles. When integrated with a light-emitting diode (LED), this device can provide real-time warning of excessive joint motions during training or other physical activities.

Unlike conventional rotary encoders strain sensor, such wearable devices are beneficial for health monitoring, due to their soft and stretchable characteristics. Moreover, this device can be rehealed when it's damaged, and can be fully recycled at room temperature, and therefore provides a reliable, economical and eco-friendly solution to wearable technologies.

Figures 2A, 2B:
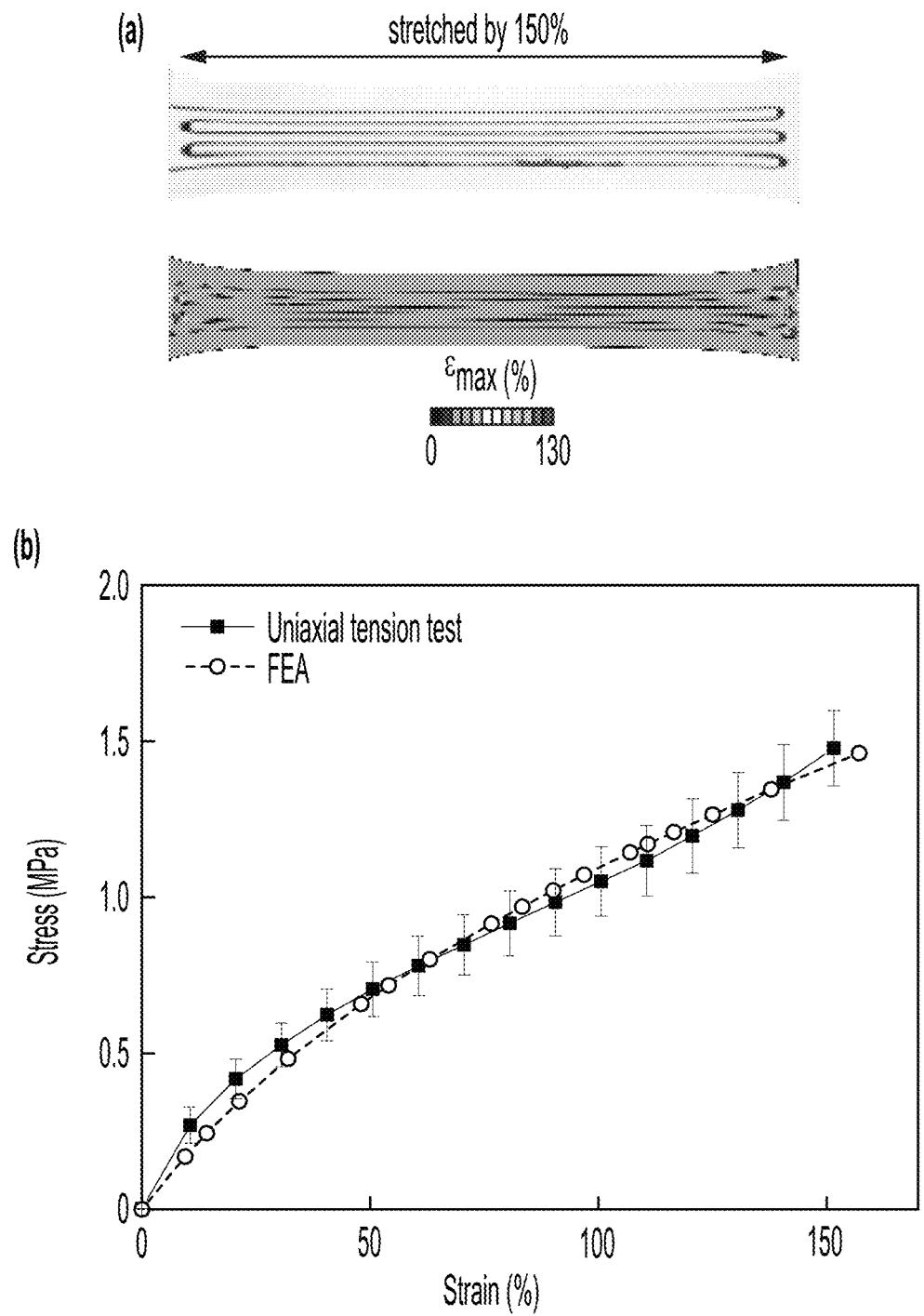
FIG. 2 (comprising Panels (a)-(g)) depicts mechanical properties of the strain sensor and amplifying circuit according to embodiments of the present disclosure. Panel (a) depicts an optical image (top subpanel) and FEA strain contour (bottom subpanel) of the strain sensor stretched by 150%. Panel (b) depicts uniaxial stress-strain curves of the strain sensor obtained from experiment and FEA. Panel (c) depicts an optical image (left subpanel) and FEA strain contour (right subpanel) of the amplifying circuit vertically stretched by 60%. Panel (d) depicts an optical image (top subpanel) and FEA strain contour (bottom subpanel) of the amplifying circuit horizontally stretched by 60%. Panel (e) depicts an optical images of the amplifying circuit at 0% strain (top subpanel), biaxially stretched by 15% (middle subpanel), and biaxially stretched by 30% (bottom subpanel). The two insets show microscope images of a chip component at undeformed and biaxially stretched by 30% states. Subpanel (f) depicts an FEA simulation model of the amplifying circuit (top subpanel), and strain contours of the amplifying circuit biaxially stretched by 15% (middle subpanel) and 30% (bottom subpanel). Panel (g) depicts an amplifying circuit reconfigured to a cylindrical shape (left subpanel depicts a top view, and middle subpanel depicts a side view). FEA simulation gives the strain contour in chip components in the cylindrical shape (right subpanel).
Figures 1, 2C, 2D, 2E, 2F:
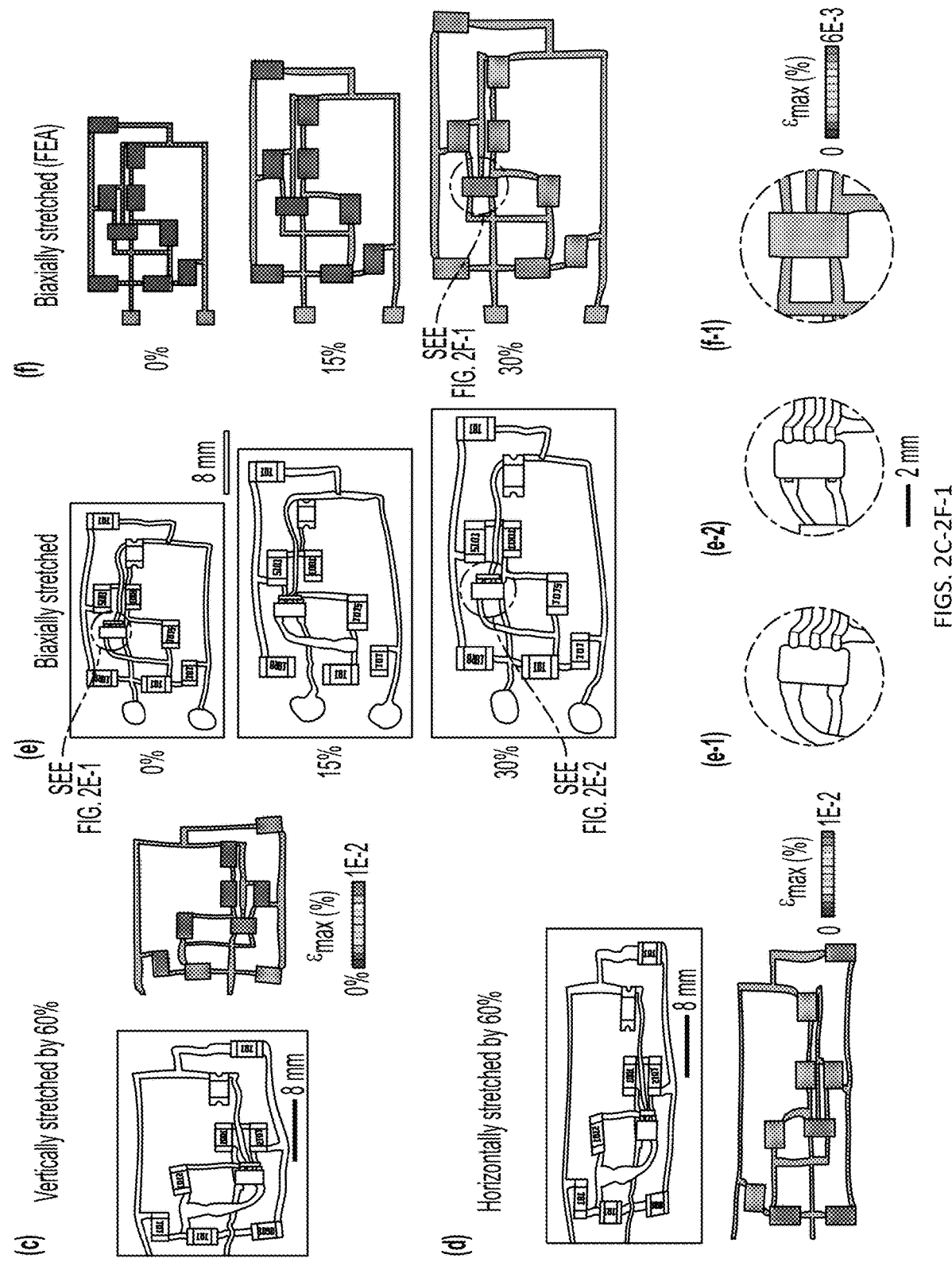
Figure 6:
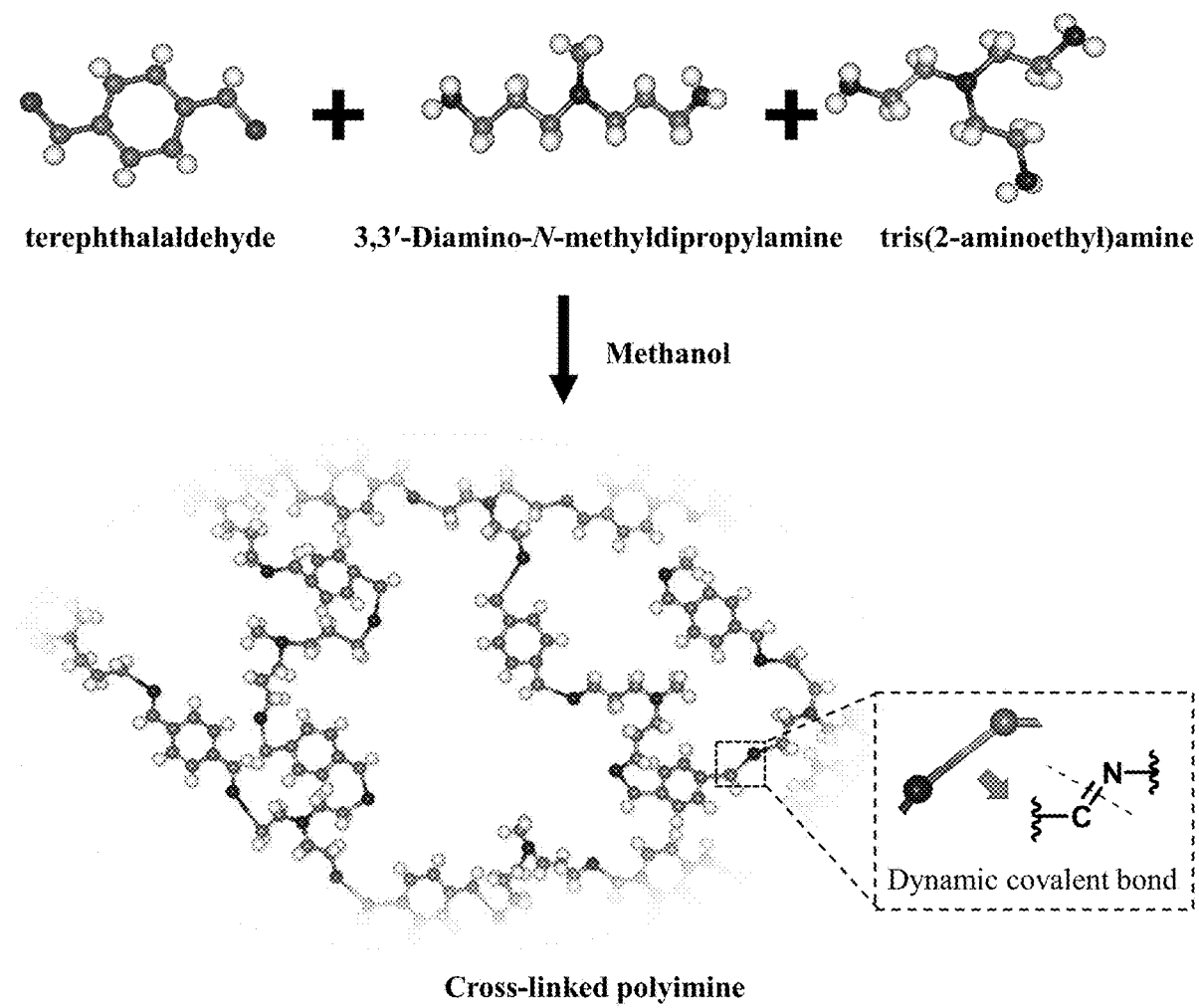
FIG. 6 depicts preparation of polymine network through imine condensation reaction.

An exploded view of the stretchable strain sensing system is shown in FIG. 1, Panel (a) to illustrate the design and construction of the device. The device can include two subsystems: the amplifying circuit and the strain sensor. The amplifying circuit incorporates liquid metal (LM) alloy as intrinsically stretchable and self-healable circuit interconnects between commercial small-scale chip components. The strain sensor can be composed of LM alloy, which in some cases can be doped with microparticles (e.g., $SiO_2$), in order to enhance strain sensitivity. Both subsystems are encapsulated by hyperelastic polyimine membranes (e.g., with Young's modulus E=2 MPa), which are synthesized by crosslinking monomers (e.g., terephthalaldehyde, 3,3'-Di-amino-N-methyldipropylamine, and tris(2-aminoethyl) amine, and the like, as depicted in FIG. 6). Conductive wires can connect the device to an external power supply.

Figure 7:
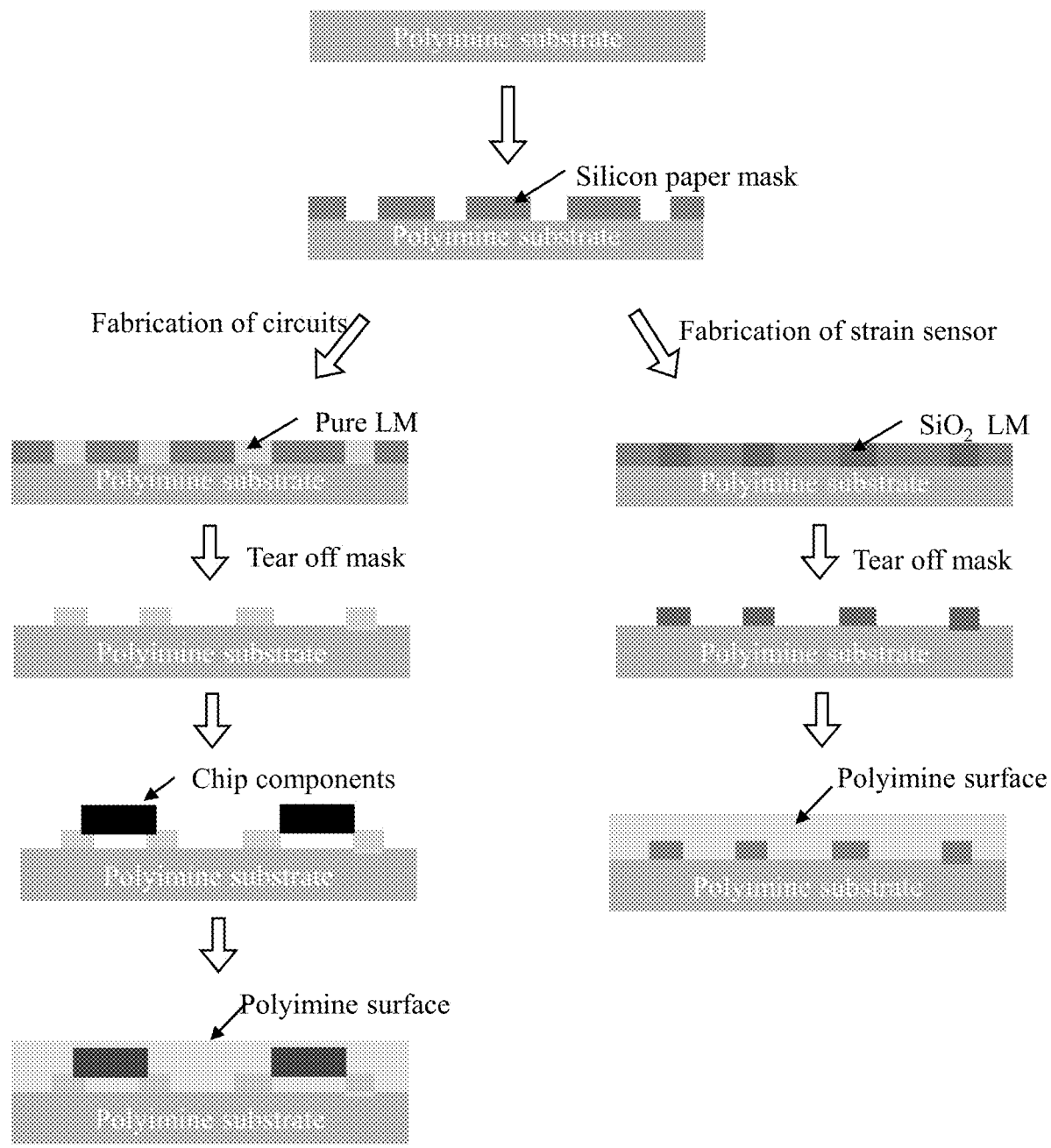
FIG. 7 depicts a schematic illustration of fabrication processes of the amplifying circuit and strain sensor according to embodiments of the present disclosure.

The detailed fabrication process is illustrated in FIG. 7. The fluidity of LM Circuitry can provide superior compliance and stretchability without sacrificing its electronic performance. Compared with serpentine interconnects widely used in stretchable electronics, the design and manufacturing of the device described herein are much simpler and more economical. The soft integrated device (as depicted in FIG. 1, Panel (b) can be bent (e.g., as shown in FIG. 1, Panel (c)) and twisted (e.g., as shown in FIG. 1, Panel (d)) while functioning. Because bond exchange reactions within the polyimine network can effectively relax residual stresses, the device has excellent malleability.

The device can be reconfigured into different shapes for different purposes. For example, FIG. 1, Panel (e) depicts the device bent into a semi-circle and kept at the new shape after stress relaxation by heating the device to 60° C. When necessary, the device can be reconfigured into other shapes, and this process is reversible.

The integrated device can be mounted around a joint, for real-time monitoring of the joint motion. As shown in FIG. 1, Panel (f), the device is attached on an elbow (top), when the bending of the elbow exceeds a predetermined threshold, the LED turns on (bottom) to warn the wearer.

Figure 2G:
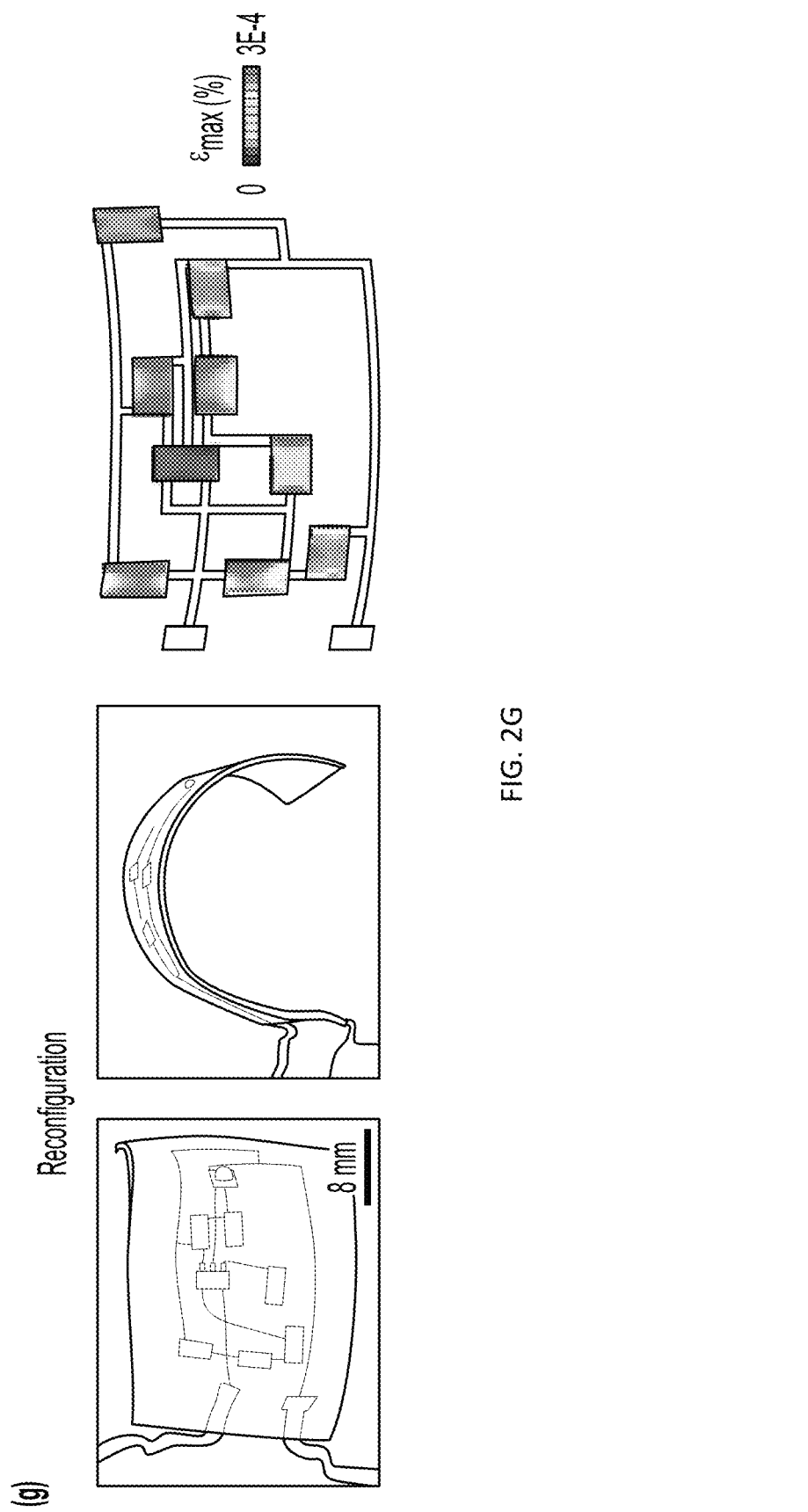
Figure 8:
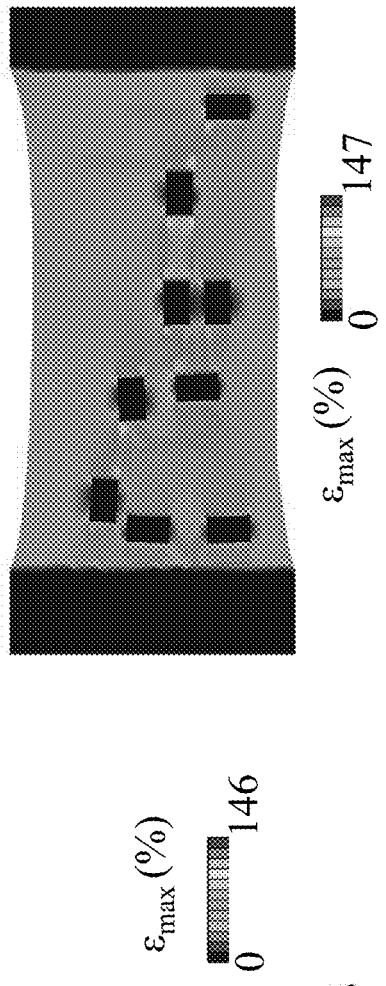
FIG. 8 (comprising Panels (a)-(d)) depicts heat graphs of max principal strain contours in polyimine when the amplifying circuit is subjected to 60% uniaxial strain along vertical (Panel (a)) and horizontal (Panel (b)) directions; 30% biaxial strain (Panel (c)), and reconfiguration (Panel (d)).
Figure 8:
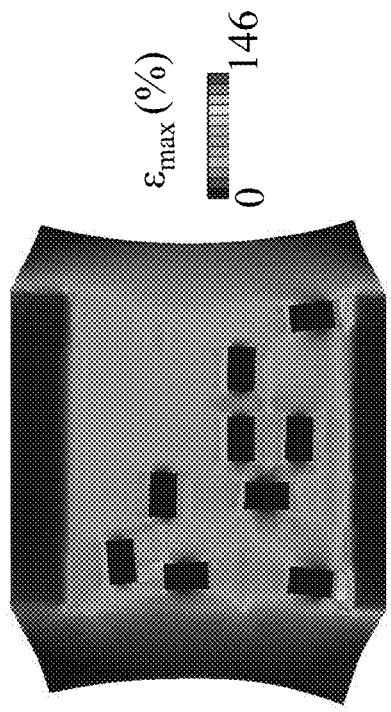
Figure 8:
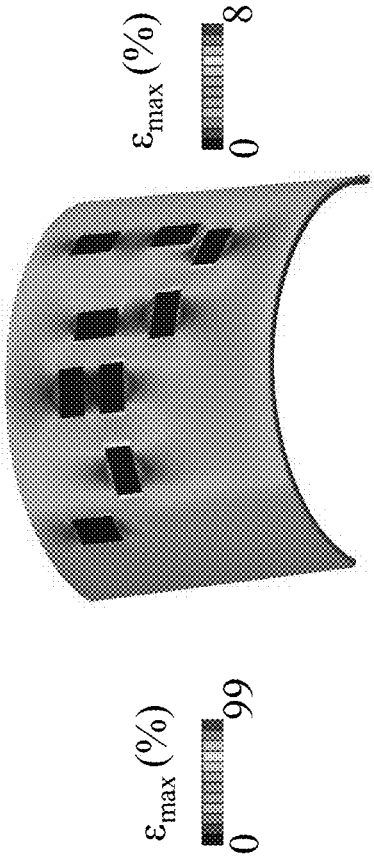
Figure 8:
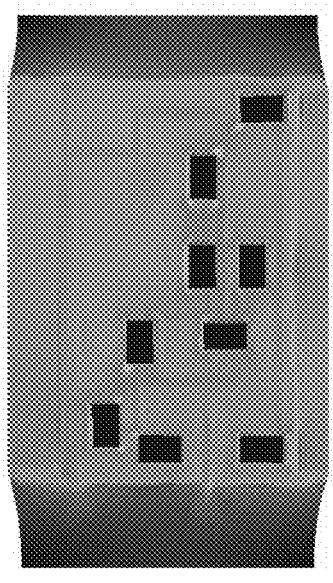
Figure 9:
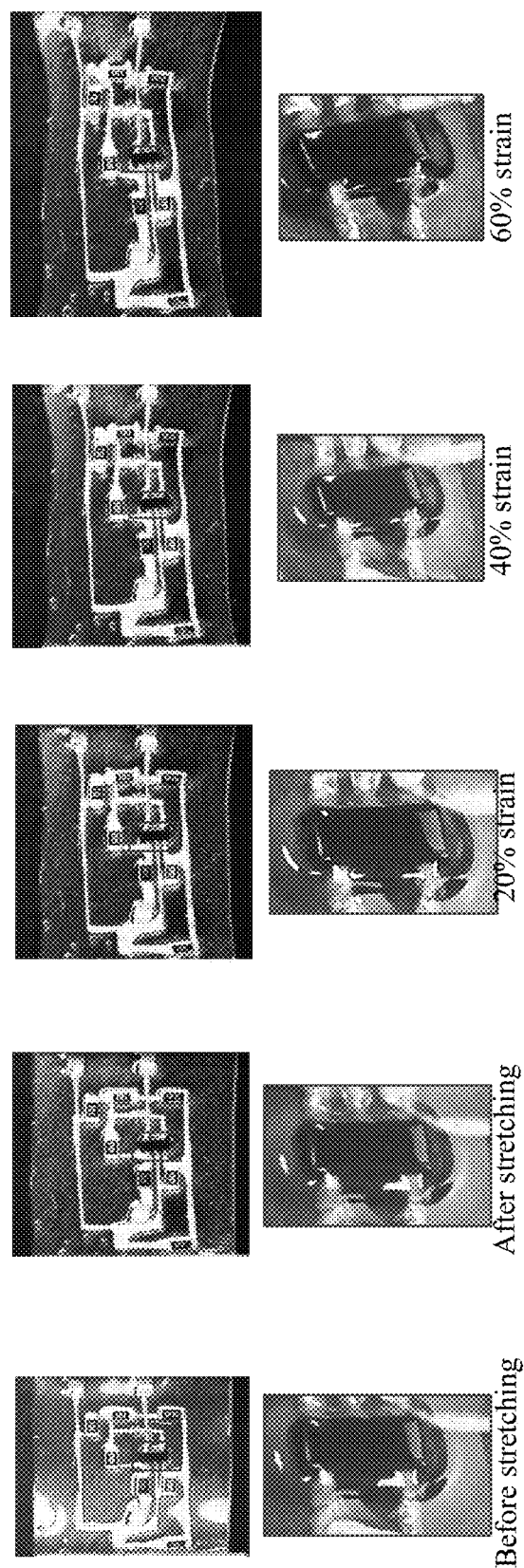
FIG. 9 depicts optical images of the amplifying circuit under uniaxial stretching. The second image shows the device after release of the strain, to illustrate reversibility in the responses. Microscope images of op-amplifier at the bottom show no signs of debonding or failure in LM interconnects.

Mechanical performance of the stretchable amplifying circuit was investigated, and the results are presented in FIG. 2, Panels (c)-(g). FIG. 2, Panels (c) and (d) show the amplifying circuit being stretched by 60% along vertical and horizontal directions, respectively. The strain contours of the chips shown in FIG. 2, Panels (c) and (d) demonstrate that the maximum strains in the chips are smaller than 0.01% even though the strains in polyimine reach ~140% (FIG. 8, Panels (a) and (b)). The maximum strains in chips are much lower than the typical failure strain of silicon (~1%), implying safe operation of the amplifying circuit under such extreme deformations. FIG. 2, Panel (e) presents optical images of the amplifying circuit when no strain (top), 15% biaxial strain (middle) and 30% biaxial strain (bottom) are applied. The enlarged microscope images of a chip component before and after application of 30% biaxial strain, as shown at the bottom of FIG. 2, Panel (e), show no signs of debonding or failure in the LM interconnects at the edges of the chip component. Enlarged microscope images of a chip component under uniaxial tension up to 60% strain are shown in FIG. 9. These results clearly manifest the robustness of the LM circuitry under extreme deformations. FEA simulation results of the amplifying circuit under biaxial stretching are presented in FIG. 2, Panel (f), which show good agreement with the corresponding experimental results in FIG. 2, Panel (e). The maximum strains in the chip components are lower than 0.006% even when the polyimine substrate experiences ~100% strain (FIG. 8, Panel (c)).

Thanks to the bond exchange reactions within polyimine network, the integrated device can be reconfigured into different shapes. As shown in FIG. 2, Panel (g), the originally flat device was mounted onto a cylinder of diameter of 27.5 mm at 60° C., and then allowed to cool down at room temperature for 10 minutes, the cylindrical shape was retained. This is because the stress induced into the polyimine network during bending was effectively relaxed due to bond exchange reactions at 80° C. This process is reversible, and can be repeated for achieving different shapes. This capability renders the integrated sensing device excellent conformability to complex surfaces without introducing excessive interfacial stresses, which is beneficial for long-term reliability. Strain contours of the chip components and polyimine obtained from FEA simulation are shown in the right frame of FIG. 2, Panel (g) and Panel (d), respectively.

Figure 3A:
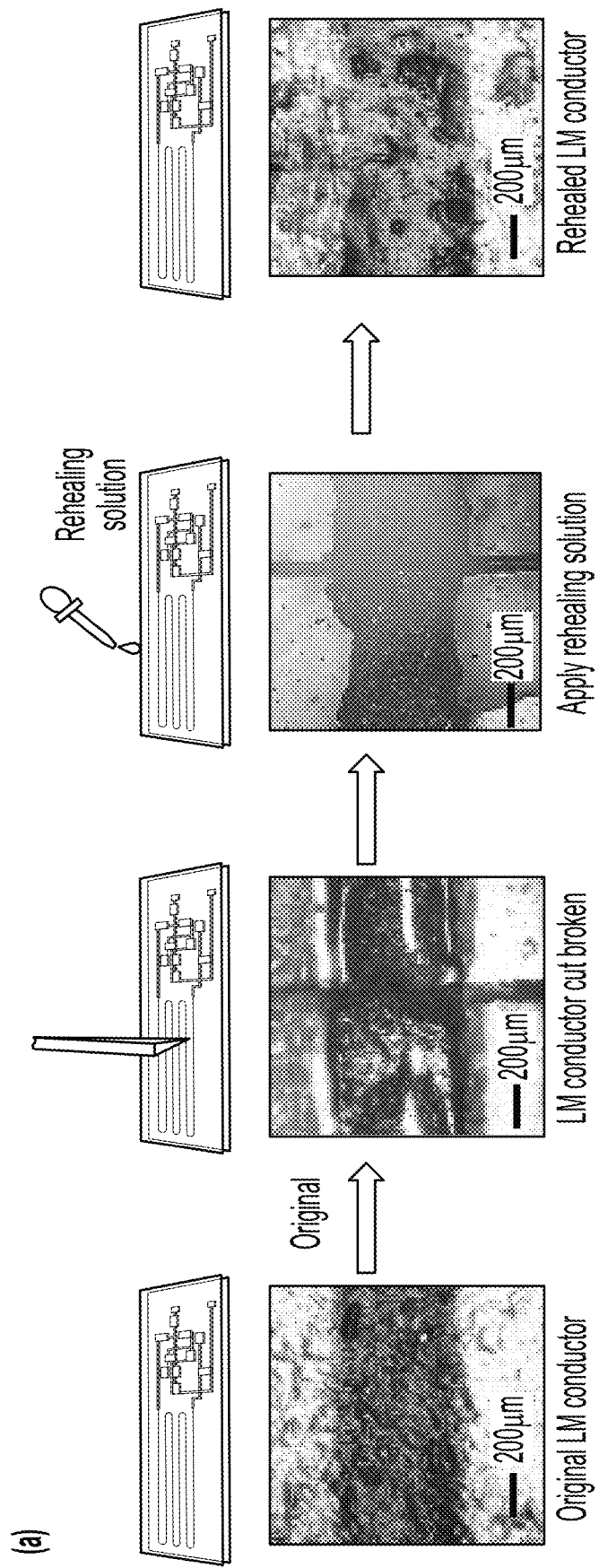
FIG. 3 (comprising Panels (a)-(c)) depicts rehealing and recycling processes of the device according to embodiments of the present disclosure. Panel (a) depicts a schematic illustration (top subpanels) and experimental microscope images (bottom subpanels) of the rehealing process. Panel (b) depicts a schematic illustration of the recycling process. Panel (c) depicts optical images of the recycling of an amplifying circuit.
Figures 3B, 3C:
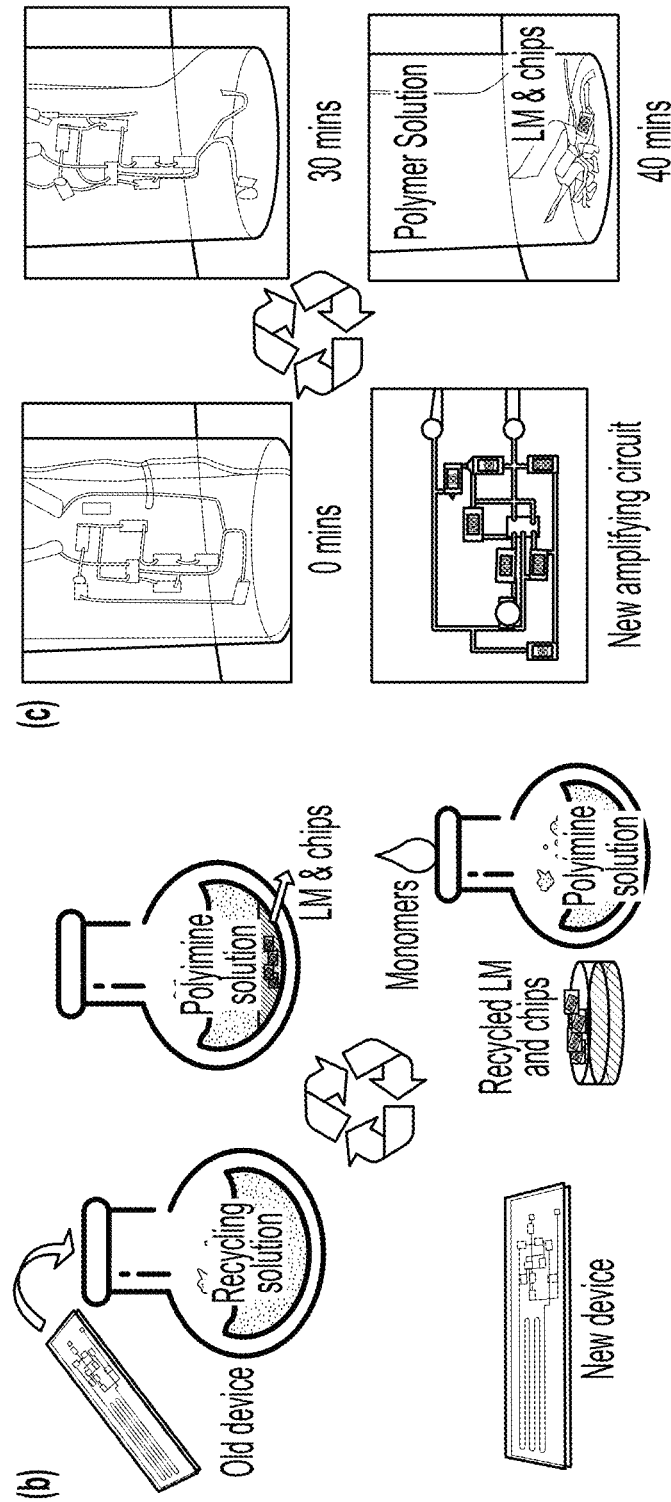

Because of bond exchange reactions within the polyimine network and flowability of LM, the integrated strain sensor has excellent rehealability when it's damaged. FIG. 3, Panel (a) illustrates the detailed rehealing process of a LM conductor encapsulated by polyimine, with schematics shown at the top and experimental optical microscope images shown at the bottom. An original LM conductor (first frame) is cut broken by a razor blade, and the crack has a width of ~80 μm, as shown by the microscope image (second frame). After applying a drop of rehealing solution (e.g., the same formula as polyimine solution) at the cut (third frame) and heat press (8.5 KPa at 80° C. for 10 mins), the interface is rehealed, and no sign of crack can be seen even under microscope (fourth frame). The rehealing process in polyimine can generate new oligomers/polymers across the broken interfaces and leads to covalent (chemical) bonding of the two pieces of polyimine. This process mimics healing of human skin, and no interfaces exist at the cut area after rehealing. This mechanism is intrinsically different from bonding two parts together using glue, which generates physical bonding (van der Waals interactions) at the interface and usually leads to significant degradation in mechanical properties.

The whole integrated sensor can be completely recycled without leaving any waste. The recycling process of an amplifying circuit is schematically illustrated in FIG. 3, Panel (b), and FIG. 3, Panel (c) shows optical images of the experiment. The process starts with immersing the old device in the recycling solution (3,3'-Diamino-Nmethyldipropylamine (0.417 g, 2.87 mmol) and tris(2-aminoethyl) amine (0.084 g, 0.574 mmol) in methanol) (top left, FIG. 3, Panels (b) and (c)). Excessive free primary amine groups in the recycling solution react with the imine-linked network through transimination, which leads to increased end groups and reduced molecular weight. This causes depolymerization of polyimine into oligomers/monomers that are soluble in the solvent, and LM and chip components sink to the bottom (top right, FIG. 3, Panels (b) and (c), and bottom right, FIG. 3, Panel (c)). Both LM and chip components can be easily separated from the solution (bottom right, FIG. 3, Panel (b)).

Figure 10:
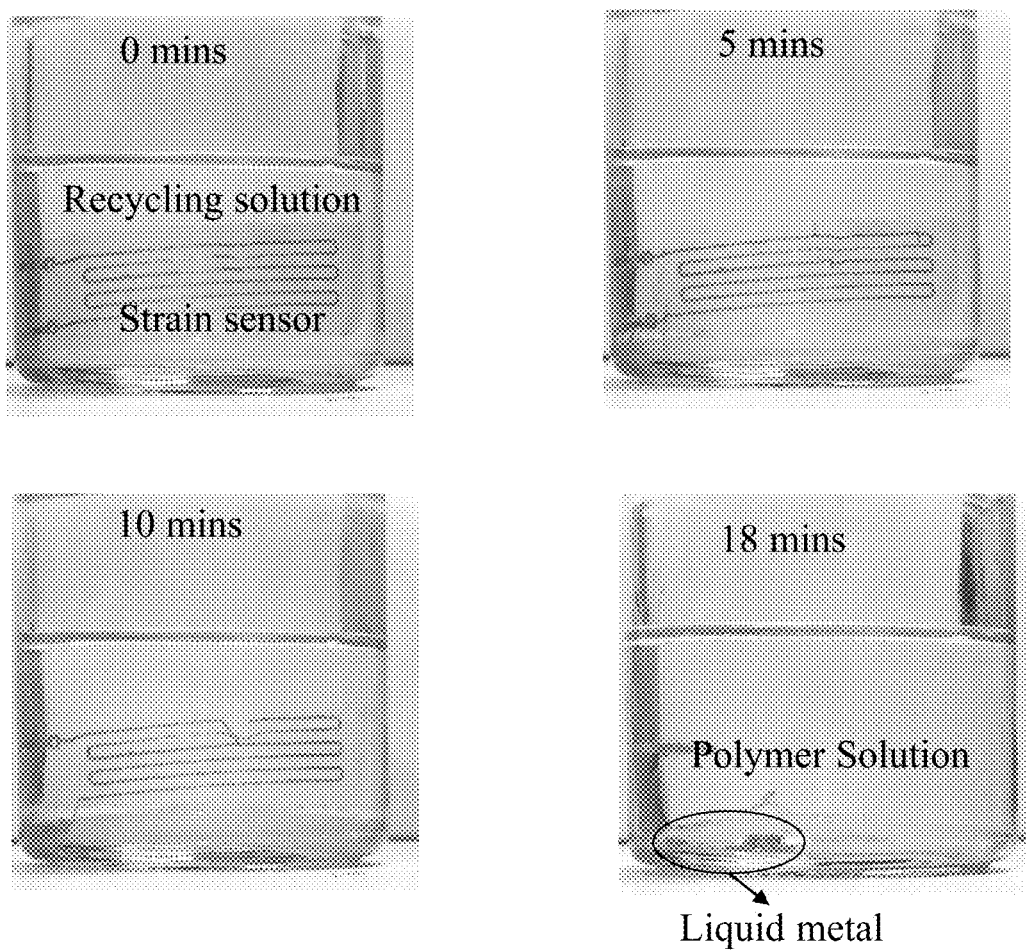
FIG. 10 depicts optical images of a recycling process of the strain sensor.

Then terephthalaldehyde can be proportionally added into the recycled solution for synthesis of new polyimine. The recycled polyimine, LM and chip components can be reused for making a new device (bottom left, FIG. 3, Panels (b) and (c)). The recycling of a strain sensor is demonstrated in FIG. 10. The recycling processes can be completed within 40 mins and 18 mins at room temperature for the amplifying circuit and strain sensor, respectively.

Figures 4A, 4B, 4C, 4D:
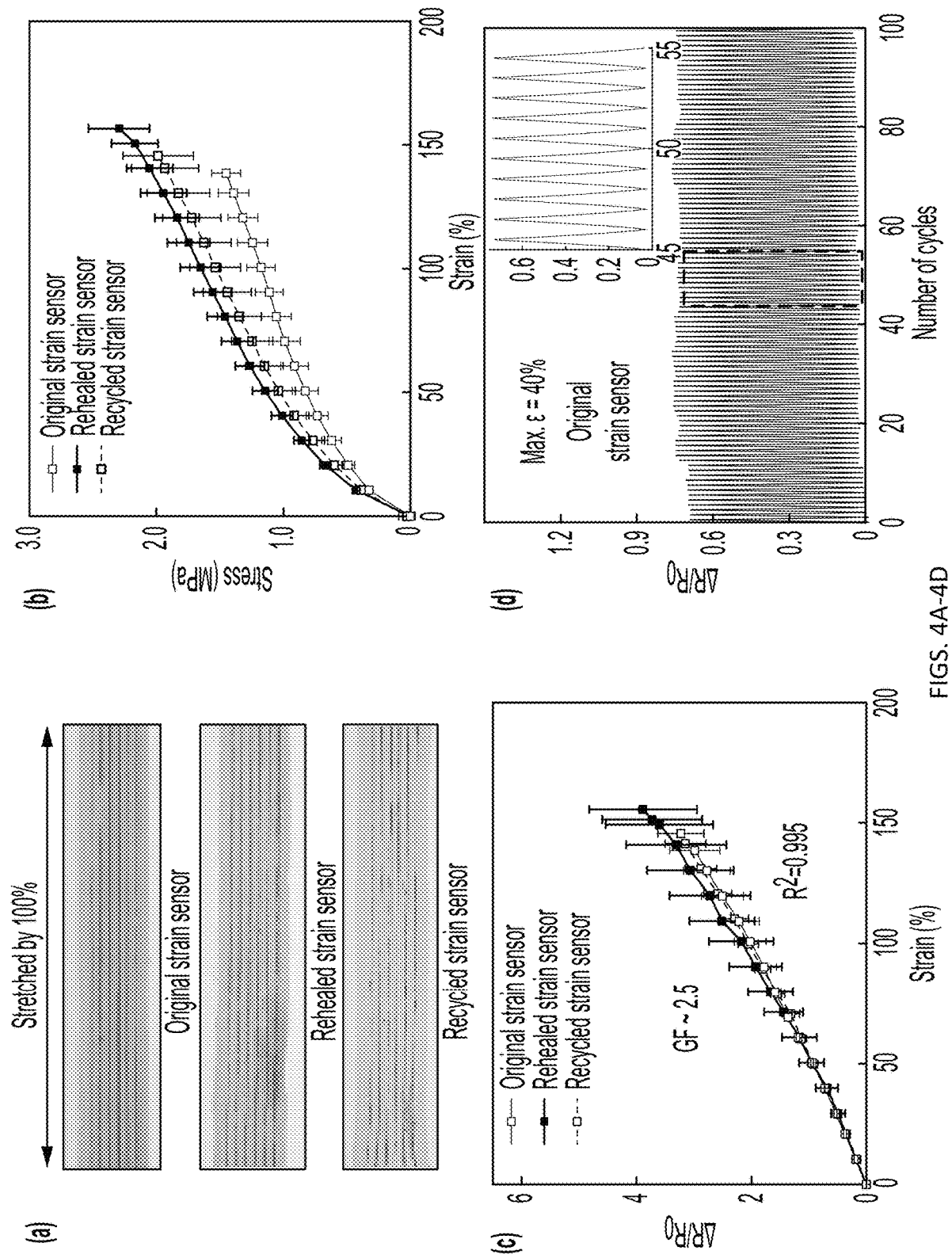
FIG. 4 (comprising Panels (a)-(f)) depicts characterization graphs of the rehealed and recycled strain sensor. Panel (a) depicts optical images of the original (top subpanel), rehealed (middle subpanel) and recycled (bottom subpanel) strain sensor stretched by 100%. Panel (b) depicts stress-strain curves of the original, rehealed and recycled strain sensors. Panel (c) depicts relative resistance change $\Delta R/R_0$ of the original, rehealed and recycled strain sensors versus applied uniaxial strain. Relative resistance change $\Delta R/R_0$ of the original are depicts in Panel (d), rehealed in Panel (e), and recycled in Panel (f), of the strain sensor under cyclic loading. The maximum strain is 40%. The insets exhibit magnified views of 10 cycles between cycle numbers 45 and 55.
Figures 4E, 4F:
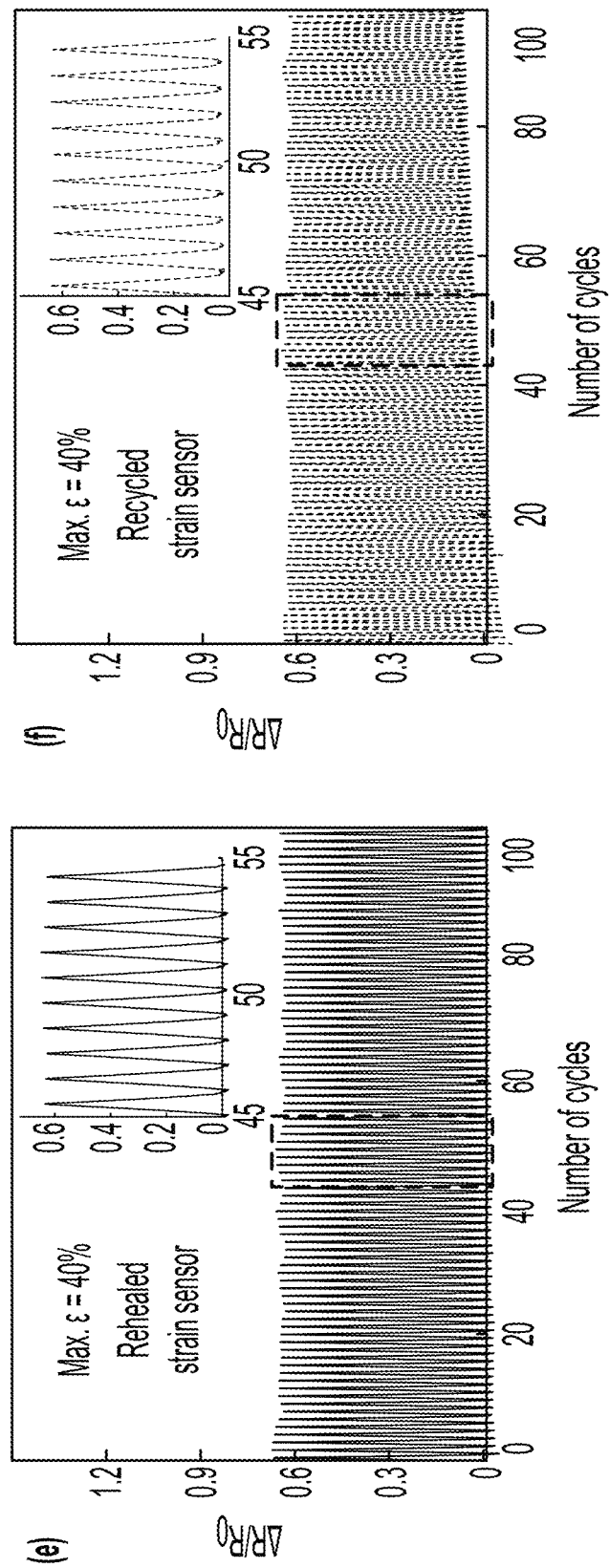
Figure 5A:
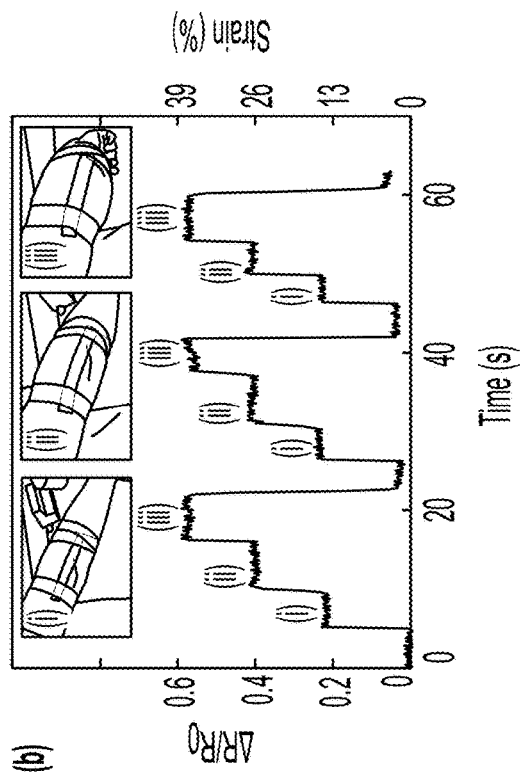
Figure 5B:
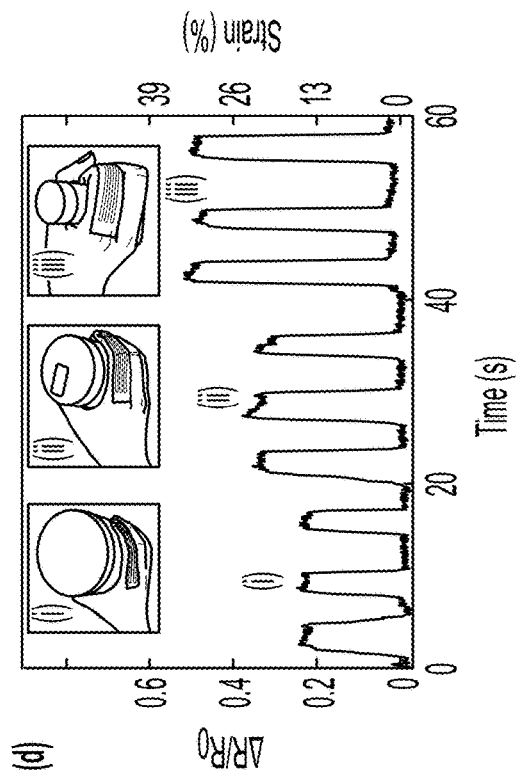
Figure 5C:
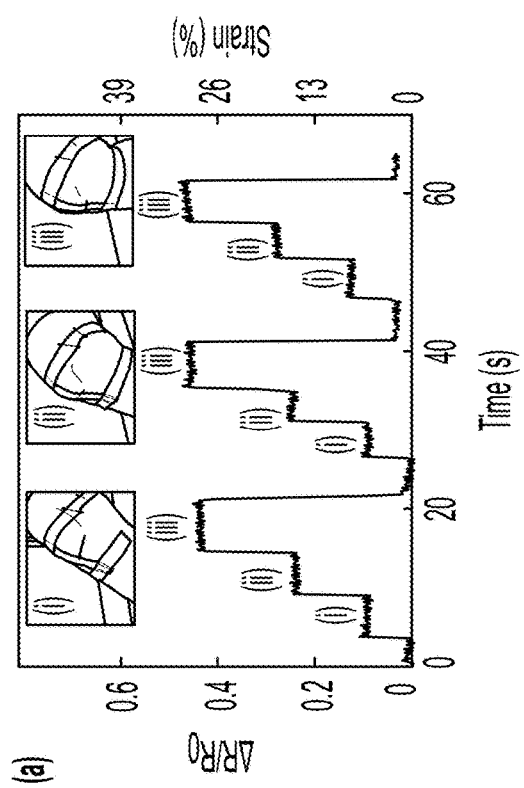
Figure 5D:
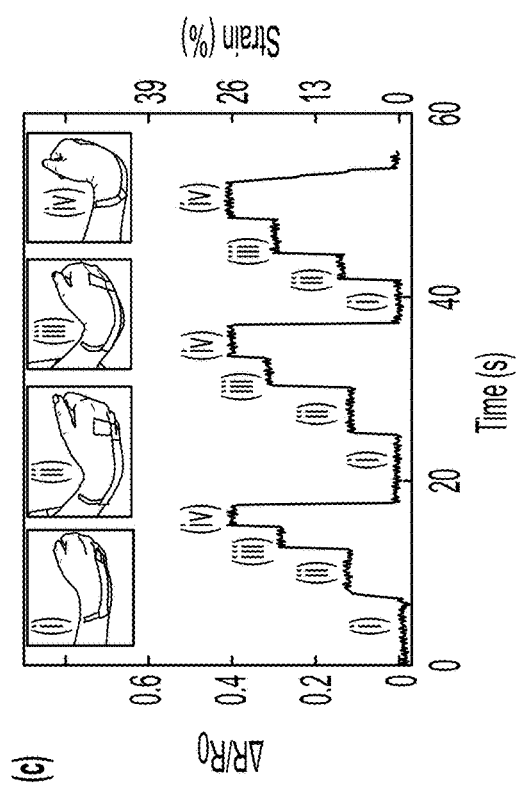
Figures 5E, 5F, 5G:
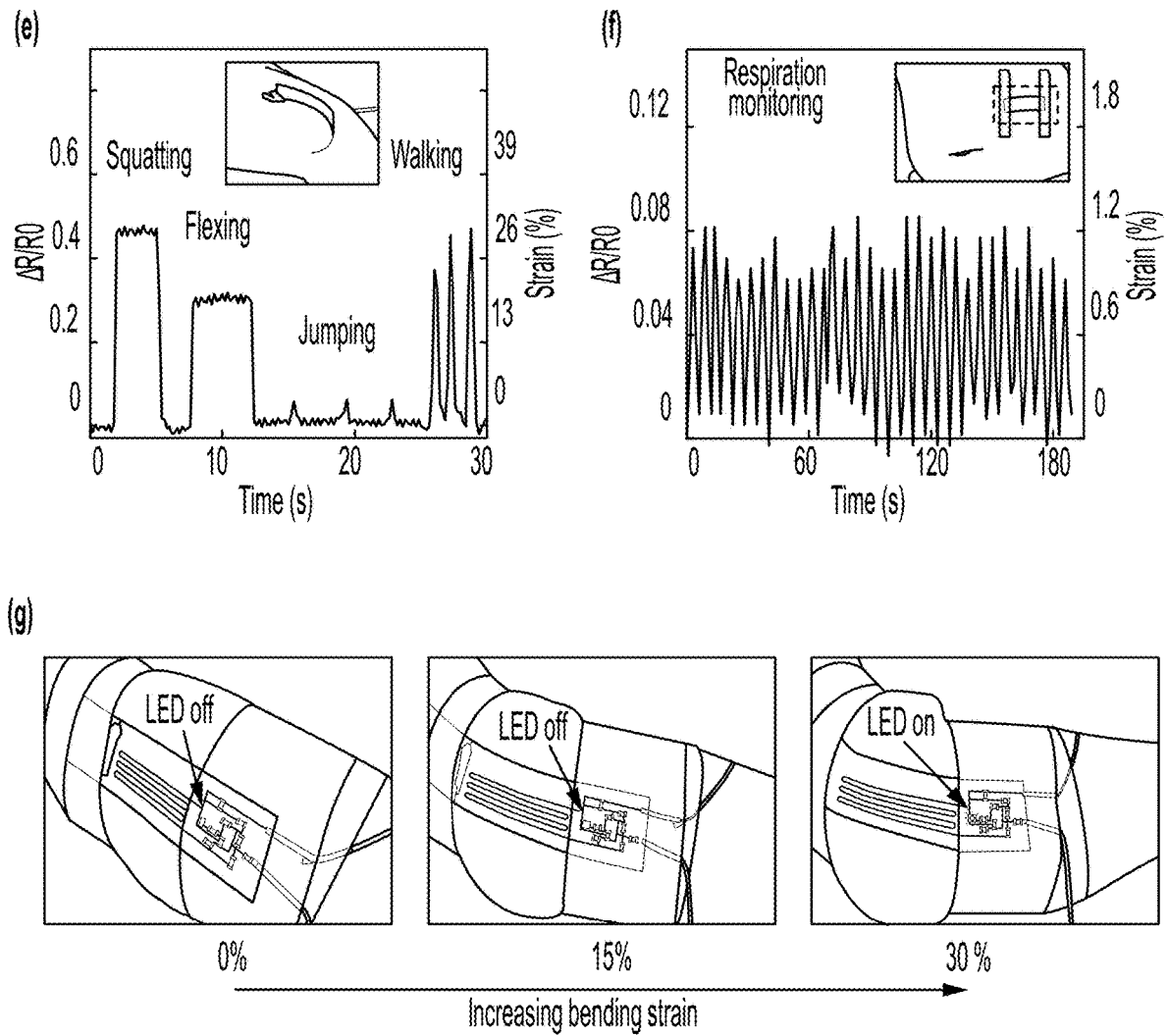

FIG. 4 compares the mechanical and electrical properties of the original, rehealed and recycled strain sensors. As shown in FIG. 4, Panel (a), the rehealed and recycled strain sensors can be stretched by 100%, without mechanical failures. Stress-strain curves of the original, rehealed and recycled strain sensors are presented in FIG. 4, Panel (b), and show comparable mechanical behavior under uniaxial stretching. FIG. 4, Panel (c) compares the relative resistance change ΔR/R0 of the original, rehealed and recycled strain sensors due to uniaxial strain, and no noticeable differences can be observed. FIG. 4, Panel (d) shows the relative resistance change ΔR/R0 of the original strain sensor under cyclic loading, with 40% maximum strain. The inset exhibits a magnified view of 10 cycles between cycle numbers 45 and 55. After 100 cycles, no significant change can be seen in its response. The results obtained from the rehealed and recycled strain sensors under the same cyclic loading conditions are presented in FIGS., Panels (e) and (f). They show comparable performance to that of the original strain sensor.

Strains on human skin can vary between ~1% on abdomen during breathing to 45% on joints during flexing, and such information can be useful for health monitoring. The compliant and stretchable strain sensor reported here can capture the full range of strains on human skin, and thus can be attached onto different parts of human body for different purposes. FIG. 5, Panel (a) demonstrates a strain sensor attached on the knee for monitoring its degree of flexion. As shown in the insets i, ii, and iii, three different bending states of knee flexion are accurately captured by the strain sensor, with the maximum tensile strain equal to 30% when the knee is at 90° angle.

The strain sensor is also attached onto the elbow and waist, and can accurately measure different strains at these joints due to different flexing states, as shown in FIG. 5, Panels (b) and (c), respectively. FIG. 5, Panel (d) shows a strain sensor attached on an index finger, and the strain information can be used to detect the size of objects held by the hand. The three insets i, ii and iii give three objects of diameters 90 mm, 58 mm and 25 mm, which correspond to the average strains of 17%, 22%, and 33% measured by the strain sensor, respectively. This capability can be applied on robots for accurate sensing of environment and delicate handling of fragile objects. When strain information is combined with frequency data, the strain sensor can provide monitoring of more complex joint motion and physical states. As shown in FIG. 5, Panel (e), four different states of knee joint motion are recorded by the strain sensor.

The squatting, flexing, jumping and walking states show significantly different signatures, when strain level, plateau width and frequency are all taken into consideration. In addition to joint motion, the strain sensor can also be applied on the abdomen for real-time monitoring of respiration. FIG. 5, Panel (f) presents respiration monitoring data obtained from the strain sensor, with a frequency of 11/minute. Such information can be used to detect abnormalities in the rate and pattern of respiration, which are a strong indicator of acute events, such as cardiac arrest, chronic obstructive pulmonary disease (COPD), pneumonia, and asthma. FIG. 5, Panel (g) shows the integrated strain sensor attached on an elbow. When the elbow is not flexing (left), or the flexion angle is small (middle), the strain detected by the strain sensor is small, and the LED stays off. When the elbow flexion angle is too large (right), the strain detected by the strain sensor exceeds the predetermined threshold, leading to the LED to turn on. This capability of real-time monitoring and warning of the strain at joints can provide assistance during joint rehabilitation.

Polymerizable Composition

In one aspect, the present disclosure provides a polymerizable composition including a dialdehyde monomer, a diamine monomer, and a triamine monomer.

In certain embodiments, the dialdehyde monomer is a compound of Formula (I):

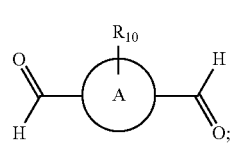

Formula (I)

wherein

represents a $C_1$-$C_{20}$ alkyl, $C_4$-$C_{10}$ heteroaryl, a $C_6$-$C_{12}$ aryl, or a $C_3$-$C_9$ cycloalkyl;

$R_{10}$ is independently a substituent at each open valence of A; and each instance of $R_{10}$ is independently selected from the group consisting of hydrogen, deuterium, $C_1$-$C_6$ alkyl, $C_1$-$C_6$ alkenyl, $C_1$-$C_6$ alkoxy, hydroxy, halogen, and combinations thereof.

In certain embodiments,

is a $C_6$-$C_{12}$ aryl. In certain embodiments,

is benzene. In certain embodiments, each instance of $R_{10}$ is hydrogen. In certain embodiments, the compound of Formula (I) is terephthaldehyde.

In certain embodiments the diamine monomer is a compound of Formula (II):

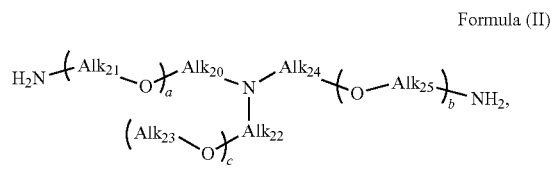

Formula (II)

wherein $Alk_{20}$, $Alk_{21}$, $Alk_{22}$, $Alk_{23}$, $Alk_{24}$, and $Alk_{25}$ are each independently a $C_1$-$C_{12}$ alkyl, optionally substituted with deuterium, $C_1$-$C_6$ alkenyl, $C_1$-$C_6$ alkoxy, hydroxy, halogen, and combinations thereof; and a, b, and c are each independently an integer from 0 to 5.

In certain embodiments, $Alk_{20}$ and $Alk_{24}$ each represent an unsubstituted $C_3$ alkyl. In certain embodiments, $Alk_{20}$ and $Alk_{24}$ each represent —$(CH_2)_3$—. In certain embodiments, $Alk_{22}$ represents an unsubstituted $C_1$ alkyl. In certain embodiments, $Alk_{22}$ represents —$CH_3$. In certain embodiments, a, b, and c are each 0. In certain embodiments, the compound of Formula (II) is 3,3'-diamino-N-methyldipropylamine.

In certain embodiments, the triamine monomer is a compound of Formula (III):

Formula (III)

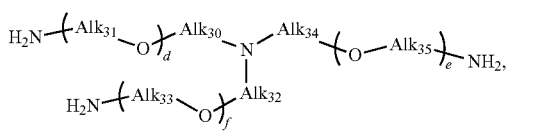

where
Alk$_{30}$, Alk$_{31}$, Alk$_{32}$, Alk$_{33}$, Alk$_{34}$, and Alk$_{35}$ are each independently a C$_1$-C$_{12}$ alkyl, optionally substituted with deuterium, C$_1$-C$_6$ alkenyl, C$_1$-C$_6$ alkoxy, hydroxy, halogen, and combinations thereof; and d, e, and f are each independently an integer from 0 to 5.

In certain embodiments, Alk$_{30}$, and Alk$_{32}$, and Alk$_{34}$ each represent an unsubstituted C$_2$ alkyl. In certain embodiments, Alk$_{30}$, and Alk$_{32}$, and Alk$_{34}$ each represent —(CH$_2$)$_2$—. In certain embodiments, d, e, and f are each 0. In certain embodiments, the compound of Formula (III) is tris(2-aminoethyl)amine.

In certain embodiments, the composition includes a ratio of between about 1:1 to about 1:0.4 mmol of dialdehyde monomer to diamine monomer. In certain embodiments, the composition includes a ratio of between about 1:1 to about 1:0.6 mmol of dialdehyde monomer to diamine monomer. In certain embodiments, the composition includes a ratio of between about 1:1 to about 1:0.8 mmol of dialdehyde monomer to diamine monomer. In certain embodiments, the composition includes a ratio of between about 1:0.7 to about 1:0.05 mmol of dialdehyde monomer to triamine monomer. In certain embodiments, the composition includes a ratio of between about 1:0.5 to about 1:0.05 mmol of dialdehyde monomer to triamine monomer. In certain embodiments, the composition includes a ratio of between about 1:0.4 to about 1:0.05 mmol of dialdehyde monomer to triamine monomer. In certain embodiments, the composition includes a ratio of between about 1:0.3 to about 1:0.1 mmol of dialdehyde monomer to triamine monomer. In certain embodiments, the composition includes a ratio of between about 1:0.7 to about 1:0.05 mmol of diamine monomer to triamine monomer. In certain embodiments, the composition includes a ratio of between about 1:0.5 to about 1:0.05 mmol of diamine monomer to triamine monomer. In certain embodiments, the composition includes a ratio of between about 1:0.4 to about 1:0.05 mmol of diamine monomer to triamine monomer. In certain embodiments, the composition includes a ratio of between about 1:0.3 to about 1:0.1 mmol of diamine monomer to triamine monomer. In certain embodiments, the composition includes a ratio of between about 1:1 to about 1:0.8 mmol of terephthaldehyde to 3,3'-diamino-N-methyldipropylamine, a ratio of between about 1:0.3 to about 1:0.1 mmol of terephthaldehyde to tris(2-aminoethyl)amine, and a ratio of between about 1:0.3 to about 1:0.1 mmol of 3,3'-diamino-N-methyldipropylamine to tris(2-aminoethyl)amine.

In some embodiments, the polymerizable composition includes an organic solvent. Exemplary organic solvents include, but are not limited to, diethylether, dichloromethane, chloroform, benzene, toluene, methanol, ethanol, isopronanol, n-butanol, pentanes, hexanes, acetone, acetonitrile, DMF, DMSO, ethyl acetate, and combinations thereof. In certain embodiments, the polymerizable composition includes methanol.

In certain embodiments, the polymerizable composition is polymerized to form a polyimine. In certain embodiments, the polyimine is synthesized by stirring components of the polymerizable composition described elsewhere herein in an organic solvent described elsewhere herein. In some embodiments, the polyimine is synthesized by stirring terephthaldehyde, 3,3'-diamino-N-methyldipropylamine, and tris(2-aminoethyl)amine in methanol.

Polyimine Composition

In another aspect, the present disclosure relates to a polyimine formed from the polymerizable composition described elsewhere herein. In certain embodiments, the polyimine is a crosslinked polyimine. In certain embodiments, the polyimine crosslinks are based on the dynamic covalent chemistry principle where the polyimine undergoes an imine bond exchange reaction. In some embodiments, the imine bond exchange reaction occurs at room temperature. In other embodiments, the imine bond exchange reaction occurs at elevated temperatures (e.g., temperatures above room temperature).

In certain embodiments, the solvent used during the polymerization reaction is removed from the resulting polyimine and a polyimine film is formed. In some embodiments, the film is formed by heat pressing the polyimine at an elevated temperature under pressure. In certain embodiments, the polyimine film is formed by heat pressing the polyimine at about 80° C. and about 8.5 kPa for about 12 hours. Although not wishing to be limited by theory, it is believed that the imine bond exchange reaction that the polyimine undergoes lead to effective stress relaxation. In some embodiments, the effective stress relaxation leads to excellent malleability and reprocessibility. Although not wishing to be limited by theory, it is believed that the imine bond exchange reaction can occur at the interface of two polyimine films (e.g. at the interface of a cut in a previously intact polyimine film), producing new covalent boding across the interface and therefore leading to interfacial bonding or healing.

In some embodiments, the polyimine undergoes a transimination reaction when excessive diamine and/or triamine monomers are introduced. Therefore, in some embodiments, the polyimine depolymerizes into oligomers and/or monomers that are soluble in an organic solvent described elsewhere herein. In certain embodiments, the oligomers and/or monomers formed in the depolymerization reaction can be used in repeated polymerization reactions to reform the polyimine. In some embodiments, the polyimine can be 100% recycled to form a new polyimine that has substantially identical properties as a "fresh" polyimine which was not made from recycled polymerizable monomers. In certain embodiments, an amount of the dialdehyde monomer is added to the oligomers and/or monomers formed from the depolymerization reaction in order to have the desired ratio between monomers for polymerization. In certain embodiments, the desired ratio of dialdehyde monomer to diamine monomer and triamine monomer is a ratio described elsewhere herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Polyimine Preparation

The polyimine was synthesized by mixing terephthalaldehyde (0.5 g, 3.72 mmol, Combi-Blocks), 3,3'-Diamino-N-methyldipropylamine (0.417 g, 2.87 mmol, Sigma-Aldrich), and tris(2-aminoethyl)amine (0.084 g, 0.574 mmol, Oakwood Chemical) in methanol as shown in FIG. 6. The solution was vigorously stirred and poured into a silicone paper mold, followed by evaporating in a fume hood for 6 hours at room temperature and heat-pressing at 80° C. and 8.5 kPa for 12 hours.

LM Preparation

The pure LM used as interconnects is eutectic metal alloy consisting of gallium (75%) and indium (25%) (eGaIn, Sigma-Aldrich), which maintains liquid state at room temperature (melting point 15.7° C.) and has a resistivity of $29.4 \times 10^6$ $\Omega$/cm. In order to increase the resistivity of LM for improved strain sensitivity, the eGaIn was mixed with 6% wt $SiO_2$ microparticles (40 μm diameter, Sigma-Aldrich), and stirred in air at 500 rpm for 2 mins and at 2000 rpm (vigorously stirred) for 8 mins. As a result, we can get $SiO_2$ doped LM with a resistivity of $95 \times 10^{-6}$ $\Omega$/cm and suitable viscosity composed of eGaIn metal, gallium oxide and 6% wt $SiO_2$ nanoparticles.

Fabrication and Characterization of Stain Monitoring Device

Figure 11:
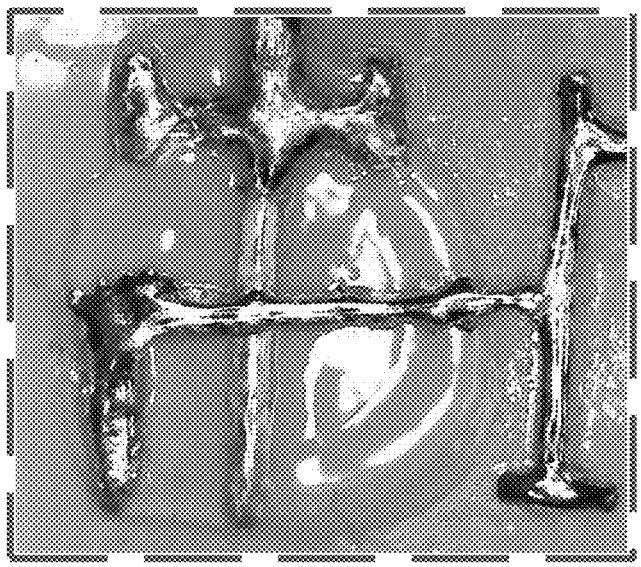
FIG. 11 depicts an amplifying circuit without chip components (left subpanel). Enlarged microscope image shows details of intersections of LM wires (right subpanel).
Figure 11:
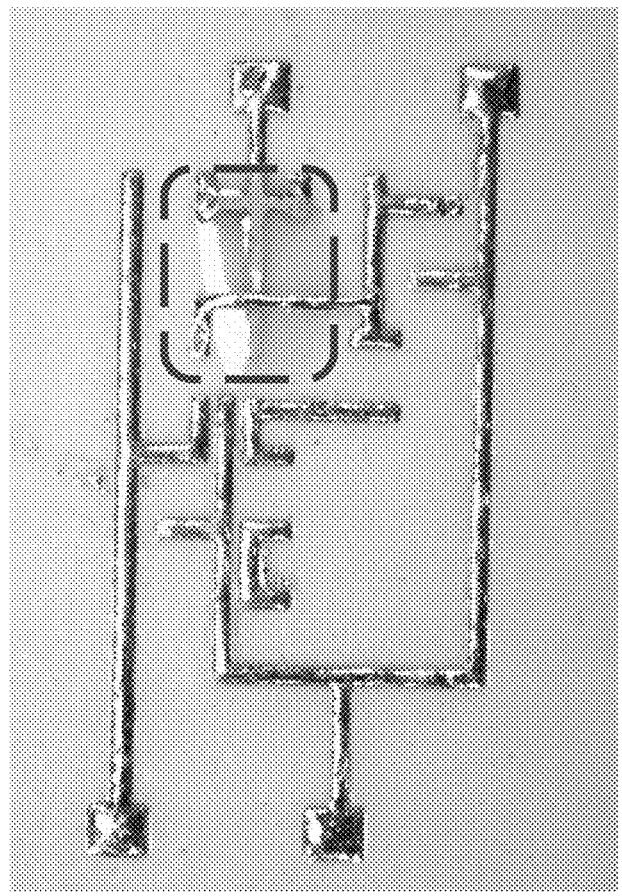

As shown in FIG. 7, a silicon paper mask, made by laser cutting (Lide laser cutting machine) a 0.2 mm thick silicone paper film (Ruspepa non-stick silicone paper), was laminated over a weakly adhering polyimine membrane substrate, and pure and $SiO_2$ doped LM were dispensed over the circuit and sensor mask, respectively. Then, a razor blade was used to remove excessive materials. Cooling down to below 15.7° C. led to solidification of LM. And removal of the mask left LM to be printed on the polyimine membrane. The commercial chip components were placed onto the designated locations manually, with the placement accuracy assured using an optical microscope. Pouring the same formula polyimine solution over the entire device encapsulated the liquid metal and chips. After curing at room temperature, the integrated device was obtained. At intersection, insulating polyimine was used to separate two LM interconnects (FIG. 11). Moreover, two copper wires were used to connect the device to an external power source.

Reheating and Recycling Process

To reheal polyimine films, a small drop of rehealing agent (the same formula as polyimine solution) was added to the crack, followed by heat-pressing at 80° C. and 8.5 KPa for 10 mins. To recycle polyimine films, 3,3'-Diamino-N-methyldipropylamine (0.417 g, 2.87 mmol) and tris(2-aminoethyl)amine (0.084 g, 0.574 mmol) were mixed in methanol. Such recycling solution depolymerizes the polyimine network into oligomers/monomers which can dissolve in methanol. After separating the LM and chip components from the polymer solution, terephthalaldehyde (0.5 g, 3.72 mmol) was added into the polymer solution for polymerization. Dilute hydrochloric acid can remove the oxide compounds on the surface of the LM and reunite them, then both LM and chips can be cleaned by methanol for reuse.

Tension and Cyclic Mechanical Test

Polyimine and LM strain sensor were tested using an INSTRON mechanical testing system. A loading strain rate of 0.08/s was used for quasi-static tension test until the film broke, and for cyclic test for 100 cycles. The strain sensors were prepared with dimensions 0.29 mm*18 mm*40 mm. Four-point measurement was adopted to measure their resistance change. A current supplier (HY3005M-3 Digital Control) was used for the current input, and Arduino as well as 16 ADC (ADS1115) was used for measuring the voltage every 0.1 seconds. A constant current of 10 mA was applied on the strain sensors.

FEA Simulation

FEA simulation was conducted using a commercial software package ABAQUS. The polyimine and LM interconnects were modeled as Neo-Hookean hyperelastic materials using 3D hybrid stress elements (C3D8H), and the chips were modeled as elastic material using 3D stress elements (C3D8). The material coefficients in Neo-Hookean models in ABAQUS were $C_{10}=0.3704$ and $D_1=0.9$ for polyimine, and $C_{10}=0.0017$ and $D_1=0$ for LM. The Young's moduli and Poisson's ratio in chip components were 160 GPa and 0.45.

Wheatstone Bridge and Differential Amplifying Circuit

Figure 12:
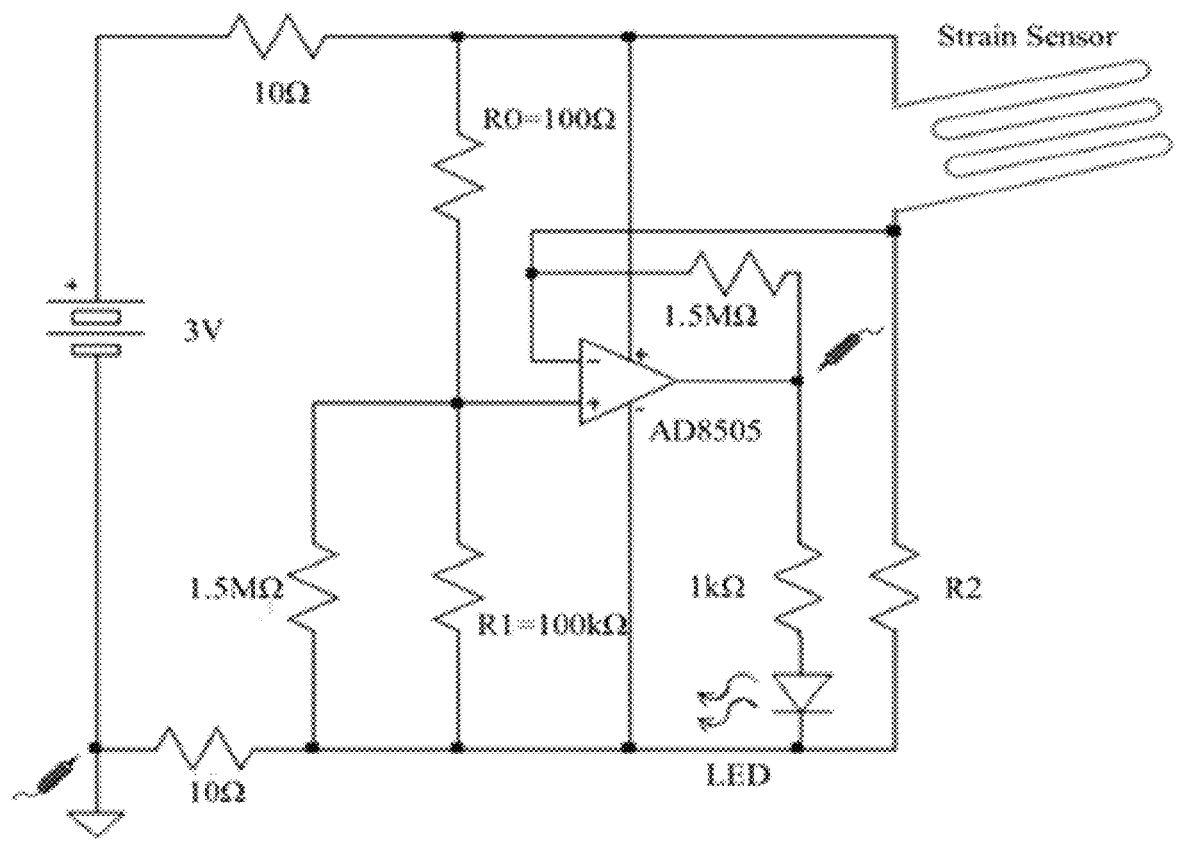
FIG. 12 depicts a Wheatstone bridge circuit and the amplifying circuit for a strain sensor according to an embodiment of the present disclosure.
Figure 13:
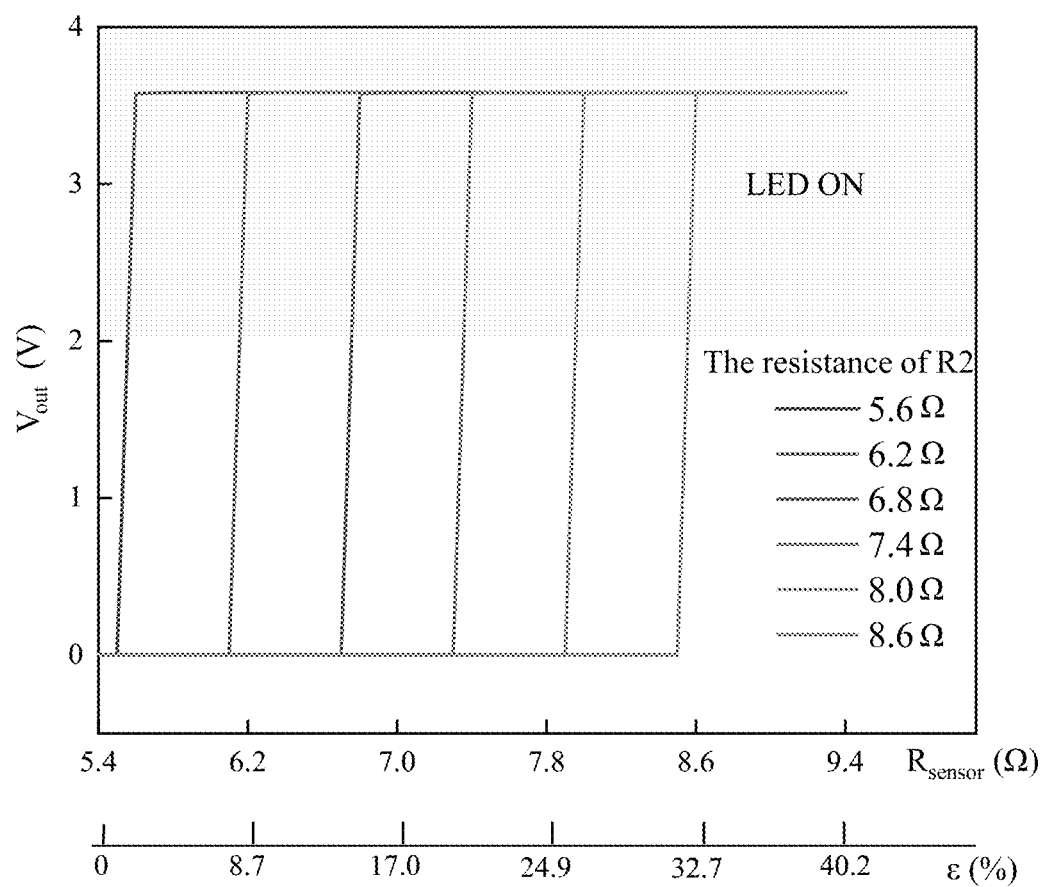
FIG. 13 depicts a graph of applied voltage and applied strain on the strain sensor according to an embodiment of the claimed invention.

In the integrated device, the resistances of LM interconnect and strain sensor were ~0.5Ω and ~5.4Ω, respectively. The on/off states for the LED are controlled by a bridge amplifier circuit composed of several resistors and an operational amplifier. The monitoring circuit was consisted of a Wheatstone bridge and a stage of differential amplification. The resistor values for three fixed arms of the Wheatstone bridge ($R_0=100Ω$, $R_1=100Ω$ and $R_2$) were determined by circuit simulation (FIG. 12). As shown in FIG. 13, the resistance of $R_2$ was selected in order to illuminate the LED at selected threshold of strain (for example: 7.4Ω resistor was selected in order to illuminate the LED at 24% strain). As a result, the sensing system can detect the strain and give a warning in real time, which can be applied to many parts of the body as shown in FIG. 5.

The resistors of the monitoring circuit (FIG. 12) were type 1206 thick film resistors (3.2 mm×1.6 mm×1.0 mm, ERJ series, Panasonic Electronic Components, USA). The amplification of the voltage offset was done by using a 5-Lead SOT-23 amplifier chip (2.9 mm×2.8 mm×1.45 mm, AD8505, Analog Devices, USA). The indicator LED (3.2 mm×1.6 mm×1.1 mm, LTST-C230KGKT, Lite-On Inc, USA) was a surface mount chip component with dimensions similar to 1206 components. The resistance values in the Wheatstone bridge and amplifier circuit were determined by a circuit simulation package (LTspice, Linear Technology Corporation, USA). The final device configuration of the respiration sensor was completed by connecting a power source or a thin lithium polymer battery (3.7 V, 45 mAh, GMB, China) to the power terminals.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

What is claimed:

1. A strain sensing device comprising:
    a volume of liquid metal (LM);
    a polyimine film encapsulating the volume of LM in a defined channel; and
    a monitoring circuit encapsulated by the polyimine film and electrically coupled to the volume of LM, wherein the monitoring circuit is configured to:
        determine a change in a property of the volume of LM; and
        identify a strain value of the polyimine film from the determined change.

2. The strain sensing device of claim 1, wherein the property of the volume of LM comprises a resistance of the volume of LM.

3. The strain sensing device of claim 1, wherein the volume of LM is doped with microparticles.

4. The strain sensing device of claim 3, wherein the microparticles are composed of silicon dioxide.

5. The strain sensing device of claim 1, wherein the monitoring circuit comprises a Wheatstone bridge.

6. The strain sensing device of claim 1, wherein the monitoring circuit is electrically coupled to the volume of LM via a set of LM leads.

7. The strain sensing device of claim 1, wherein individual components of the monitoring circuit are electrically coupled to one another with a set of LM leads.

8. The strain sensing device of claim 1, further comprising at least one LED electrically connected to the monitoring circuit.

9. The strain sensing device of claim 8, wherein the LED is configured to emit light at a predefined strain value threshold.

10. The strain sensing device of claim 1, wherein the strain sensing device is configured to be coupled to a joint of a patient.

* * * * *